(12) United States Patent
Matsuno

(10) Patent No.: US 6,605,033 B1
(45) Date of Patent: Aug. 12, 2003

(54) ENDOSCOPE

(75) Inventor: Shinichi Matsuno, Kanagawa-ken (JP)

(73) Assignee: Pentax Corporation, Tokyo (JP)

( * ) Notice: Subject to any disclaimer, the term of this patent is extended or adjusted under 35 U.S.C. 154(b) by 107 days.

(21) Appl. No.: 09/597,169

(22) Filed: Jun. 20, 2000

(30) Foreign Application Priority Data

Jun. 21, 1999 (JP) .......................................... 11-173491

(51) Int. Cl.$^7$ ................................................ A61B 1/00
(52) U.S. Cl. ...................................... 600/107; 600/106
(58) Field of Search ................................. 600/107, 106, 600/104, 101

(56) References Cited

U.S. PATENT DOCUMENTS

| | | | | |
|---|---|---|---|---|
| 4,867,138 A | * | 9/1989 | Kubota et al. ................ | 348/65 |
| 5,275,151 A | * | 1/1994 | Shockey et al. ............ | 600/106 |
| 5,460,167 A | * | 10/1995 | Yabe et al. .................. | 600/107 |
| 5,562,600 A | * | 10/1996 | Matsuno ..................... | 600/107 |
| 5,569,157 A | | 10/1996 | Nakazawa et al. | |
| 5,707,344 A | | 1/1998 | Nakazawa et al. | |

FOREIGN PATENT DOCUMENTS

| | | |
|---|---|---|
| JP | 57-60601 | 9/1980 |
| JP | 62-90602 | 6/1987 |
| JP | 6-319692 | 11/1994 |

* cited by examiner

*Primary Examiner*—Linda C. M. Dvorak
*Assistant Examiner*—Kenneth G Schopfer
(74) *Attorney, Agent, or Firm*—Greenblum & Bernstein, P.L.C.

(57) ABSTRACT

An endoscope is provided with an operation unit provided with at least one operation member, an insertion section to be inserted in a human cavity, the operation unit being connected with a proximal end of the insertion section, a direction setting table provided at a distal end portion of the insertion section, the direction setting table adjusting a direction in which a distal end of a treatment instrument inserted through an instrument-inserting channel protrudes from a distal end portion of the insertion section of the endoscope, and an operation wire that moves along the axis thereof upon operation of the operation member, the operation wire being connected to the direction setting table so that the direction setting table is moved in accordance with operation of the operation member. With this structure, the distal end portion of the insertion section and the operation unit is electrically insulated.

6 Claims, 9 Drawing Sheets

ENDOSCOPE

BACKGROUND OF THE INVENTION

The present invention relates to an endoscope, and more particularly, to an endoscope having a treatment instrument direction setting table for setting a direction in which a tip of the treatment instrument protruded from a distal end of an insertion section of the endoscope.

Generally, in side-view type endoscopes, a treatment instrument direction setting table is provided. The treatment instrument direction setting table (which will be referred to as a direction setting table hereinafter) is provided at a distal end portion of an insertion section of the endoscope. The direction setting table is used for varying a direction in which the tip end of the treatment instrument, which is inserted through an instrument-inserting channel formed through the endoscope, protrudes from the distal end portion of the insertion section. The direction set by the direction setting table can be varied, generally, by operating an operation member provided at an operation unit, which is connected to the proximal end of the insertion section. Upon operation of the operation member, an operation wire connecting the operation member and the direction setting table is operated and the direction of the direction setting table can be changed remotely.

In the endoscope having the structure as described above, if a treatment instrument, through which a high frequency current flows, is used, and if the high frequency current leaks onto the direction setting table, it may flow in the operation unit. In such a case, an operator of the endoscope may suffer burns when he/she touches metallic members such as an operation lever provided at the operation unit.

In order to avoid such a problem, in conventional endoscopes, the surface of the direction setting table and/or the surface of members which contact the direction setting table are formed of electrically insulating material. Examples of such configurations are described in Japan Utility Model Provisional Publications No. SHO 57-60601 and No. SHO 62-90602.

However, with such a structure, the direction setting table and/or the member contacting the direction setting table may not have sufficient mechanical strength and easily break and/or may require complicated manufacturing processes. Accordingly, such a structure is not suitable for practical use.

SUMMARY OF THE INVENTION

It is therefore an object of the invention to provide an improved endoscope, with which the above problem of burns due to the leakage of the high frequency current can be prevented with a structure suitable for practical use.

For the above object, according to the invention, there is provided an endoscope, which is provided with an operation unit provided with at least one operation member, an insertion section to be inserted in a human cavity, the operation unit being connected with a proximal end of the insertion section, a direction setting table provided at a distal end portion of the insertion section, the direction setting table adjusting a direction in which a distal end of a treatment instrument inserted through an instrument-inserting channel protrudes from a distal end portion of the insertion section of the endoscope, and an operation wire that moves along the axis thereof upon operation of the operation member, the operation wire being connected to the direction setting table so that the direction setting table is moved in accordance with operation of the operation member. With this structure, the distal end portion of the insertion section and the operation unit is electrically insulated.

Since the distal end portion of the insertion section is electrically insulated with respect to the operation unit, even if the electrical current leaks to a metallic member at the distal end portion of the insertion section, the electrical current never flows in the operation unit, and the operator will not suffer burns or the like.

In a particular case, the direction setting table is made of metal. Even in this case, the electrical current does not flow in the operation unit.

Optionally, the direction setting table may be held by a body member, which is made of metal, provided at the distal end portion of the insertion section, and the body member may be connected with the insertion section. In this structure, body member can be electrically isolated from members of the insertion section.

Still optionally, the operation wire is surrounded by electrically insulating material, and the operation wire is electrically insulated with respect to the operation member of the operation unit.

Further optionally, the operation wire is connected to the operation member via a link mechanism, the link mechanism including a link member connected to the operation member, and a rod member connecting the link member and the operation wire, the rod member being fitted in and guided by a tube member so as to move in an axial direction thereof.

With this structure, the tube member may be formed of insulating material.

Further, in this structure, a proximal end of the wire is secured to the rod member, the rod member being made of insulating material.

Furthermore, an O-ring is provided on the rod member, the O-ring being deformed to have an elliptic shape, a rotational movement of the rod member with respect to the tube member being prevented due to the elliptic shape of the O-ring.

BRIEF DESCRIPTION OF THE ACCOMPANYING DRAWINGS

DETAILED DESCRIPTION OF THE EMBODIMENT

Hereinafter, an embodiment of the present invention will be described with reference to the accompanying drawings.

Figure 1:
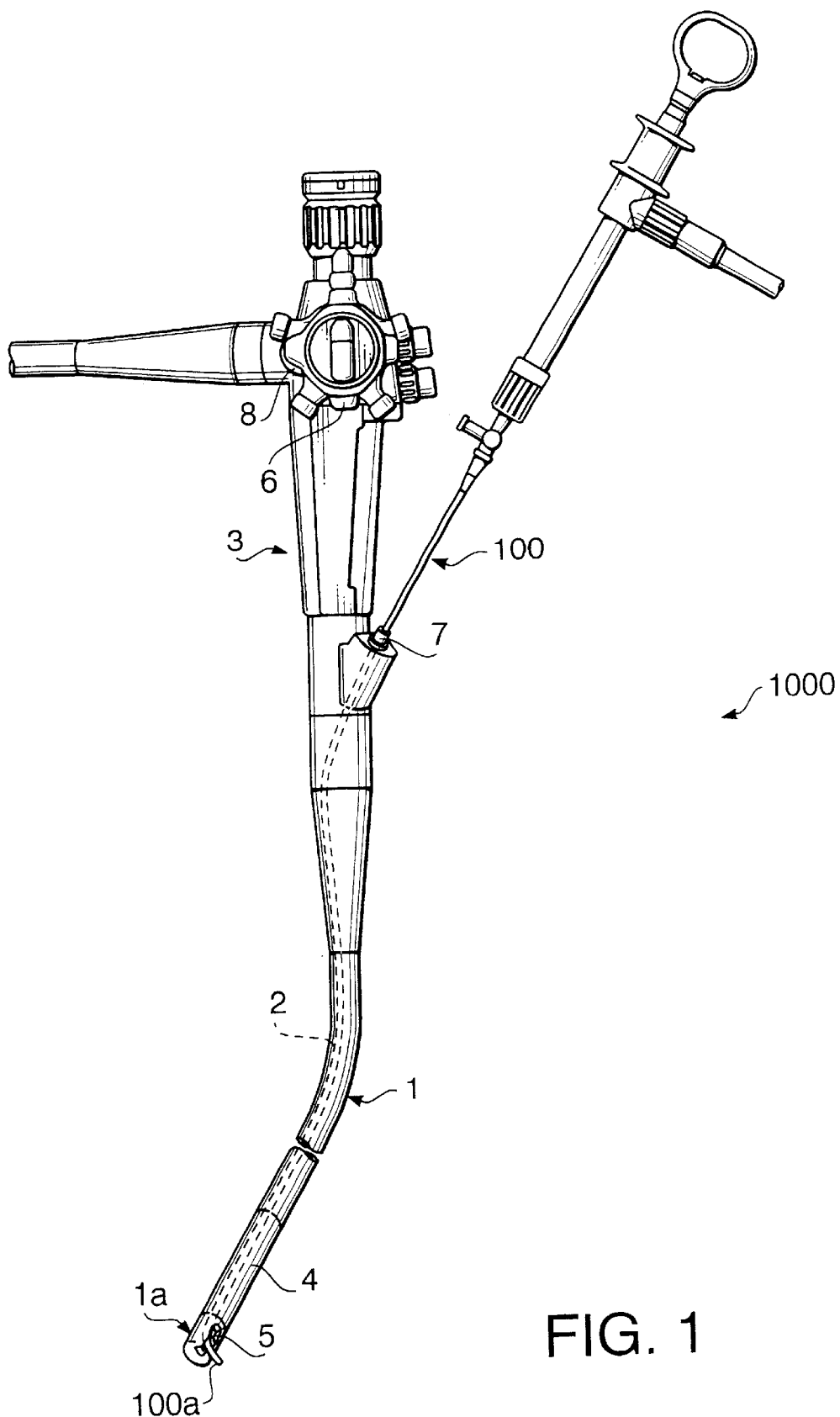
FIG. 1 shows an entire view of the endoscope according to the present invention.

FIG. 1 shows an entire view of an endoscope 1000 according to an embodiment of the present invention.

The endoscope 1000 includes an insertion section 1 to be inserted in a human cavity, and an operation unit 3 provided with operation members such as a bending knob 6 and a direction knob 8.

The insertion section 1 is formed with a bendable portion 4 at a tip end portion thereof. By operation the bending knob 3 provided on the operation unit 3, bending amount of the bendable portion 4 is changed arbitrarily and remotely.

Through the insertion section 1 and the bendable section 4, an instrument-inserting channel 2 is formed by a tube member made of electrically insulating material such as tetrafluoroethylene. A treatment instrument inlet 7 is provided at about a position where the insertion section 1 and the operation unit 3 are connected, and the proximal end of the instrument-inserting channel 2 is connected to the inlet 7. The other end of the channel 2 is located at a tip portion 1a of the insertion section 1.

Various types of treatment accessories can be inserted in the instrument-inserting channel 2. In the present embodiment, a high frequency treatment instrument 100 to which a high frequency electrical current flows when a diseased portion is to be treated is used.

A tip end 100a of the treatment instrument 100 protrudes aside at the tip portion 1a of the insertion section 1. The direction in which the treatment instrument 100 protrudes is varied/adjusted by a direction setting table 5 accommodated in the tip portion 1a of the insertion section 1. The direction setting table 5 changes the direction of the protruded treatment instrument 100 as an operation wire is proceeded/retracted by operating the direction knob 8.

Figure 2:
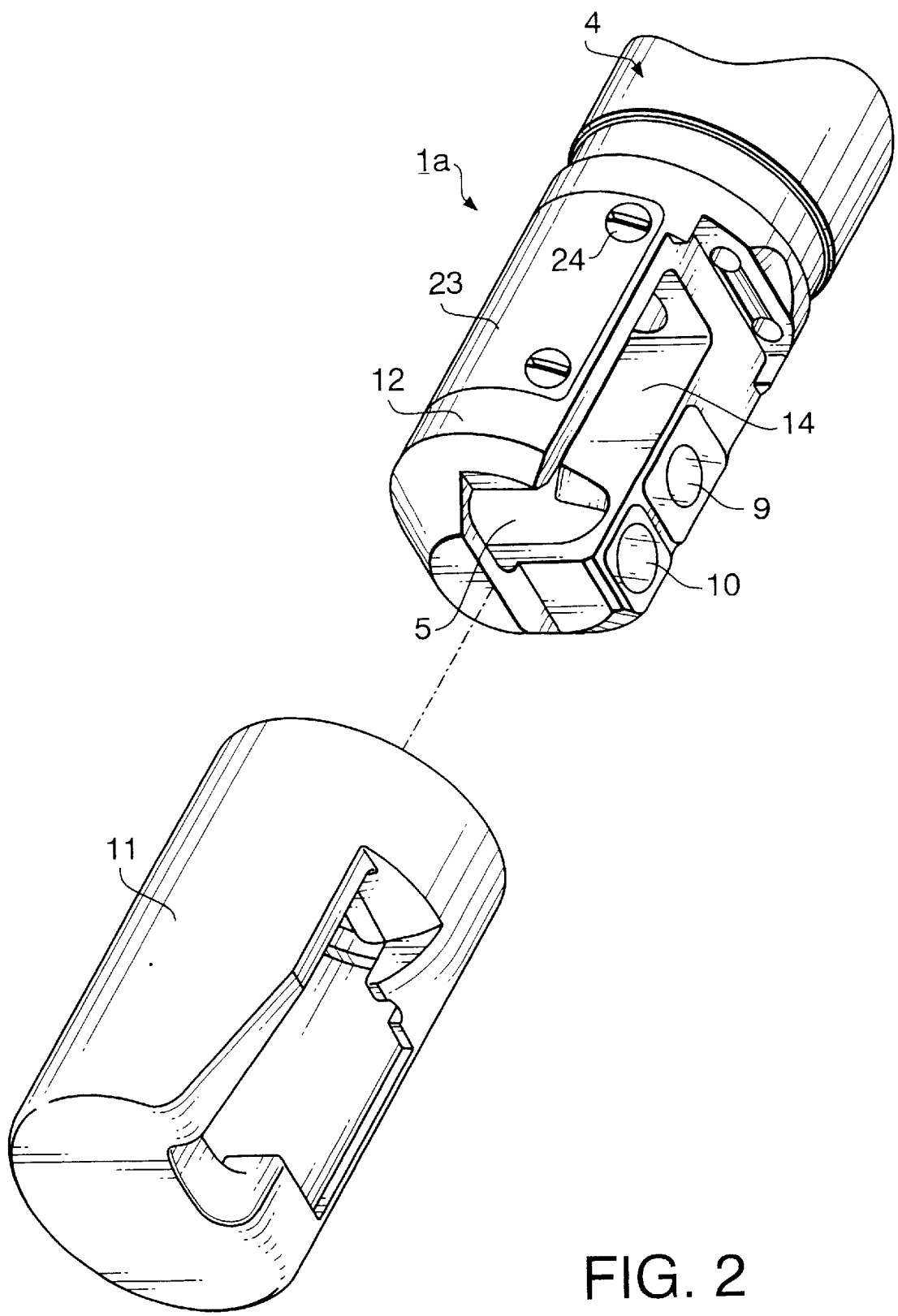
FIG. 2 is a perspective view of a tip end body and a cap member for the tip end body of the insertion section of the endoscope.

FIG. 2 is a perspective view of the tip portion 1a of the insertion section 1. In particular, FIG. 2 shows a condition in which a cap 11 is removed from a tip end body 12. The tip end body 12 is formed of stainless steel. An observation window 9, an illumination window 10 and an opening communicating a treatment instrument guide groove 14 are provided on an outer circumferential surface of the tip end body 12. The surface of the tip end body 12, except the observation window 9, the illumination window 10 and the opening 14, is covered with the cap 11. The cap 11 is formed of electrically insulating material such as fluororubber or plastic.

The endoscope according to the embodiment is a side-view type endoscope, in which the observation window 9 and the illumination window 10 are arranged at a side surface (i.e., the circumferential surface) of the tip end body 12. Next to the observation window 9 and the illumination window 10, the treatment instrument guide groove 14 is formed, and the direction setting table 5 is provided in the guide groove 14 such that the direction setting table 5 is rockable about an axis that is perpendicular to a central axis of the tip end body 12.

Figure 3:
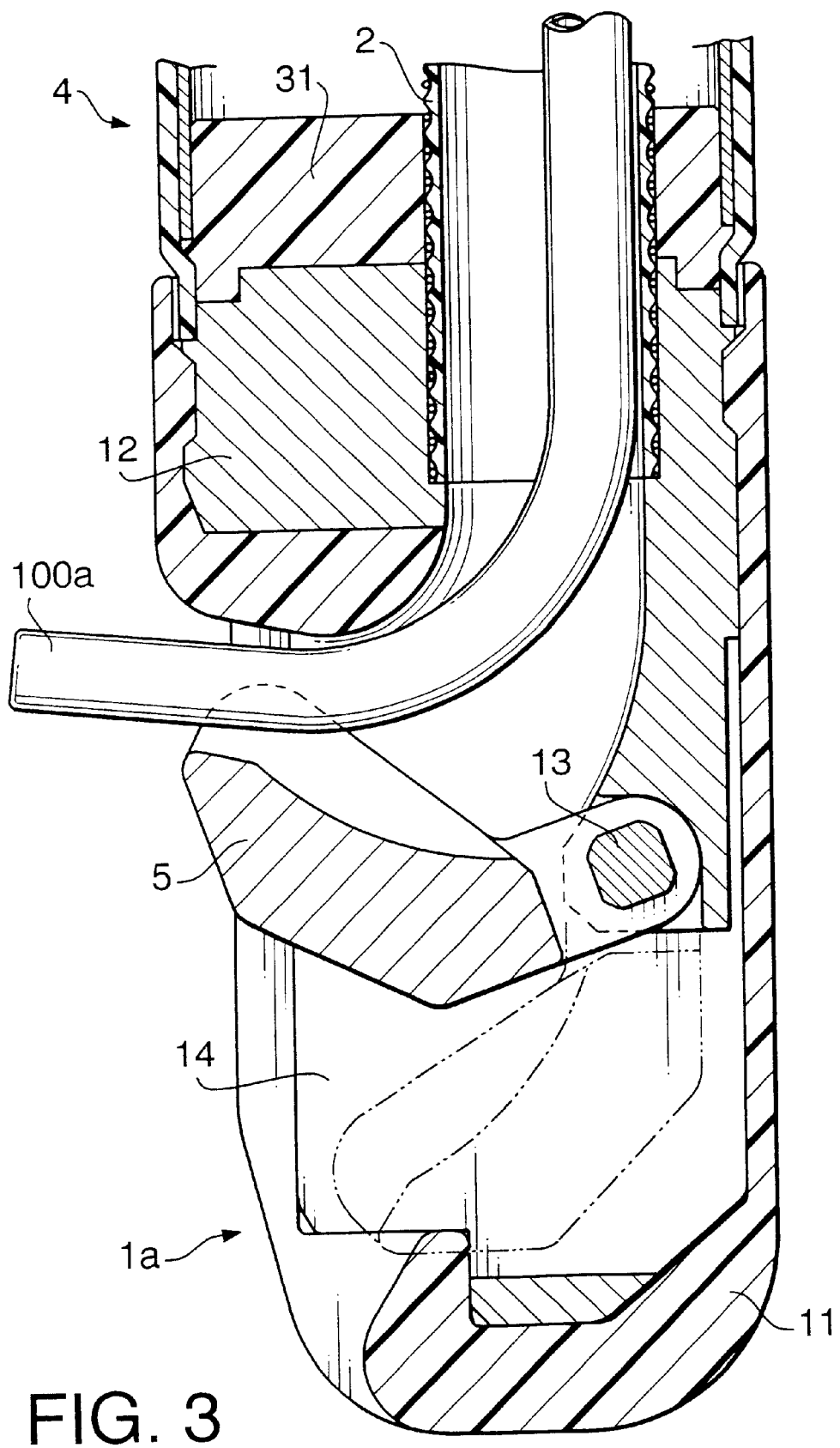
FIG. 3 is a cross sectional side view of the tip end portion of the insertion section of the endoscope.
Figure 4:
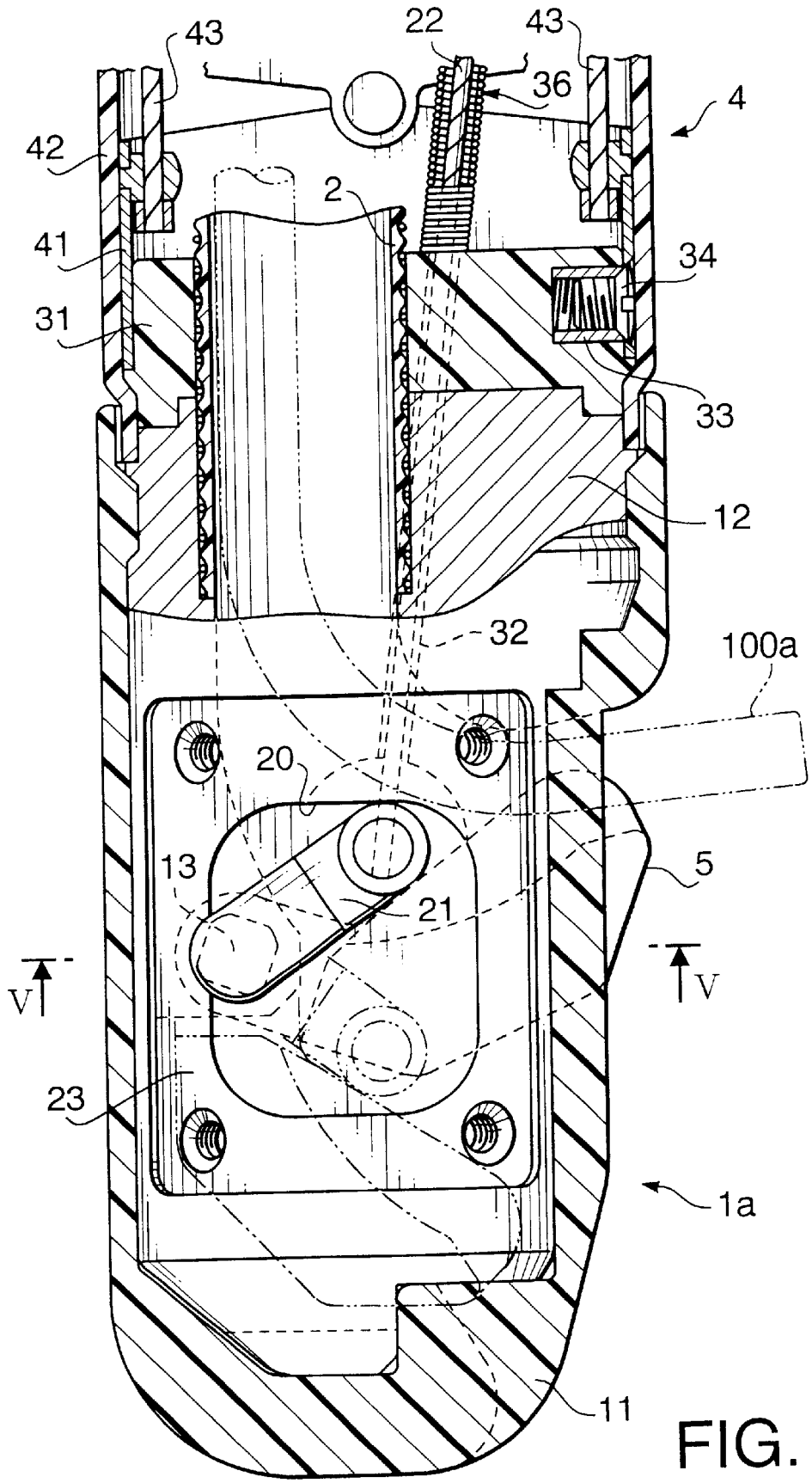
FIG. 4 is a cross sectional side view of a tip end portion of an insertion section of an endoscope according to an embodiment of the invention.
Figure 5:
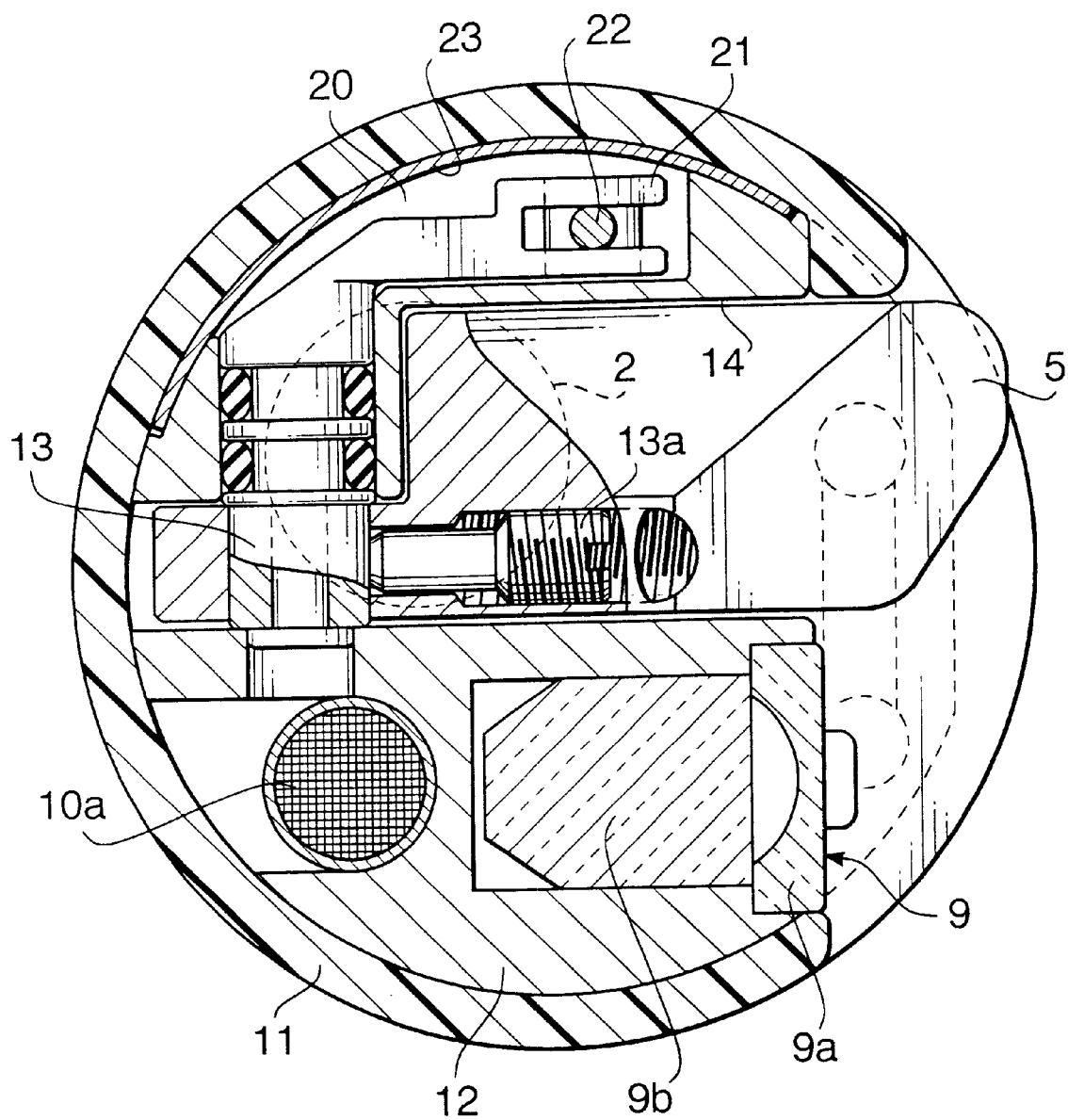
FIG. 5 is a cross sectional view, taken along line V—V of FIG. 4.

FIG. 3 is a cross sectional view of the tip end 1a of the insertion section 1 taken along a plane including the center of the guide groove 14. FIG. 4 is a cross section viewed from the opposite direction of the FIG. 3. It should be noted, however, that FIG. 4 is drawn as a composite view combining cross sectional views at various positions. FIG. 5 is a cross sectional view taken along line V—V of FIG. 4.

As shown in FIG. 5, a cover lens 9a is provided at the observation window 9, and a right-angle Dachprism (i.e., a roof prism) 9b is placed inside the observation window 9. In FIG. 5, 10a denotes a light guide fiber bundle, a light emitting end surface being located inside the illumination window 10.

The direction setting table 5 is provided in the guide groove 14, which is formed in the tip end body 12, and has a predetermined constant width. The direction setting table 5 rocks about a shaft 13.

The end of the guide groove 14 is connected with the tip end of the instrument-inserting channel 2 to communicate with each other. In the embodiment, the direction setting table 5 is formed of metal such as stainless steel, and formed as a single member. Thus, the direction setting table 5 is excellent in strength and can be manufactured easily.

On an outer side of one of walls of the tip end body 12 defining the guide groove 14, a direction setting table chamber 20 is formed as a recessed portion. In the direction setting table chamber 20, a lever 21 is accommodated. The lever 21 extends in a direction perpendicular to the shaft 13, and is integrally connected with the shaft 13.

In FIGS. 2 and 5, 23 denotes a metal plate covering an opening to the direction setting table chamber 20. As shown in FIG. 2, the metal plate 23 is secured to the tip end body 12 with four screws 24 (only two of them are shown in FIG. 2). In this embodiment, the lever 21 and the shaft 13 are also made of stainless steel.

As shown in FIG. 4, a guide hole 32 is formed from a proximal side end (i.e., a rear end) of the tip end body 12 to the direction setting table chamber 20. An operation wire 22 is inserted through in the guide hole 32 from the rear side of the tip end body 12, and the tip end of the operation wire 22 is secured to a distal end portion of the lever 21, in the direction setting table chamber 20 as shown in FIG. 5.

The shaft 13 and the direction setting table 5 are engaged such that the shaft 13, and an opening of the direction setting table 5 fitted on the shaft 13 are formed to have a substantially rectangular shape. Further, the direction setting table 5 is secured to the shaft 13 with a screw 13a.

With the above-described structure, as the operation wire 22 is moved in forward/reverse directions, the lever 21 rocks about the shaft 13, and the rocking movement of the shaft 13 is transmitted to the direction setting table 5, which rocks to change the direction of the tip end 100a of the treatment instrument 100 inserted through in the instrument-inserting channel 2.

The tip end 1a of the insertion section 1 is connected to the tip end of the bendable section 4. The bendable section 4 is formed to have a plurality of ring members, which are arranged along the axis of the bendable section 4, and each of the ring members is rotatable about an axis that is parallel to a diameter thereof. In FIG. 4, 41 denotes a distal end side member of the plurality of ring members forming the bendable section 4, 42 denotes an covering rubber tube, and 43 denotes a bending operation wire 43.

In the embodiment, the tip end body 12, which is made of metal, is not directly secured with the tip end ring member 41 of the bendable portion 4. As shown in FIG. 4, an electrically insulating block 31 is secured to the rear end of the tip end body 12 with adhesive agent, and the tip end ring member 41 is fitted on the electrically insulating block 31 and secured thereonto with screws 34. The electrically insulating block 31 is made of electrically insulating material such as polycarbonate plastic, metamorphosed PPO, or ceramics. The screws 34 are screwed in collars 33 which are planted in the insulating block 31.

With this structure, the members of the bendable section 4 and the tip end body 12 are electrically insulated completely. Therefore, even if the high frequency current leaks onto the direction setting table 5, the high frequency current does not flow in the bendable section 4.

As shown in FIG. 4, a wire guide 36 is formed throughout the entire length of the insertion section 1 including the bendable section 4. The operation wire 22 is inserted through the wire guide 36 such that the operation wire 22 is movable along the axis thereof.

Figure 6:
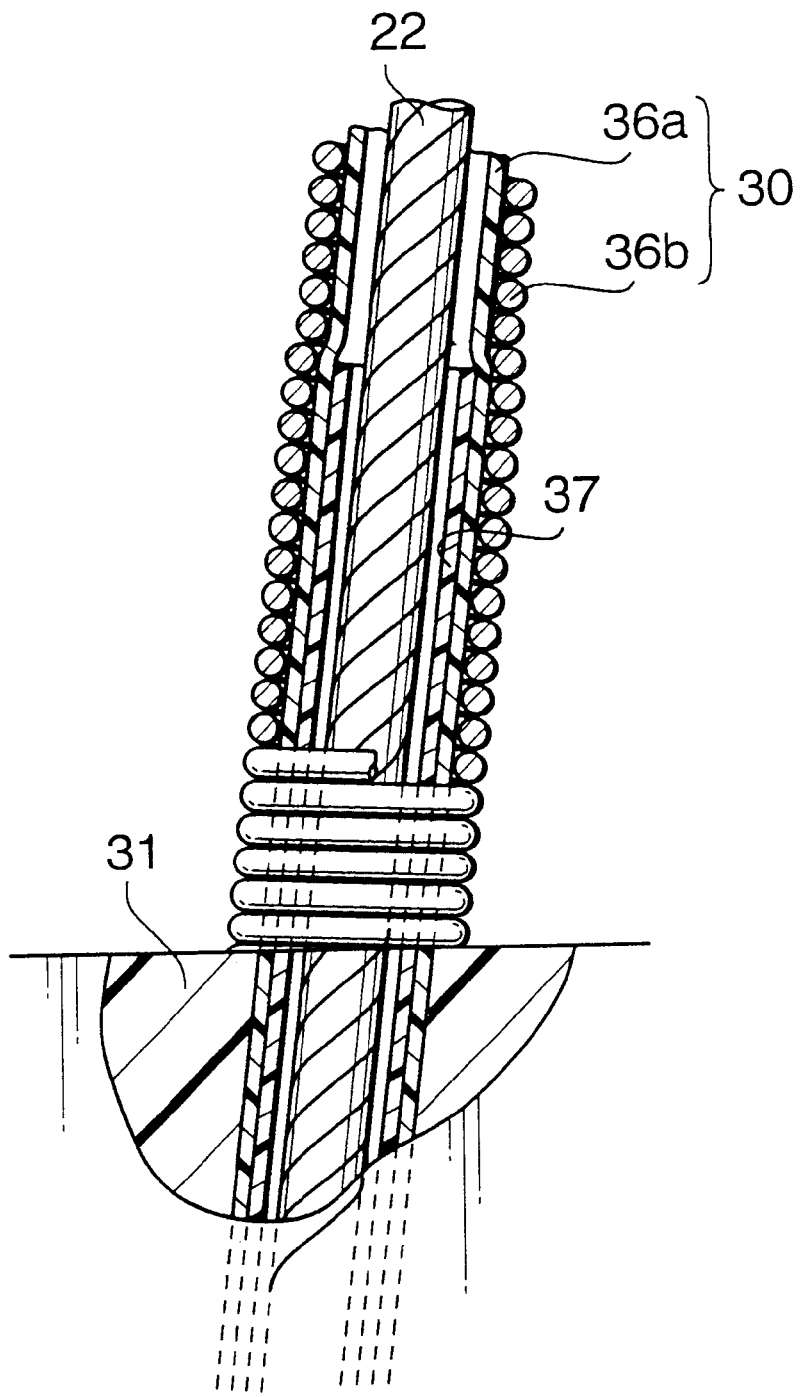
FIG. 6 is an enlarged partial cross sectional view of a wire guide.

FIG. 6 shows a position where the wire guide 36 is secured to the insulating block 31.

The wire guide 36 is formed such that an electrically insulating tube 36a is inserted through in a coil pipe 36b which is formed by closely winding a stainless steel wire at a predetermined diameter. The tube 36a is formed of, for example, tetrafluoroethlene.

The tip end of the wire guide 36 is connected with a connection tube 37 by adhesive agent. The connection tube 37 penetrates through the tip end body 12. An end portion of the connection tube 37 is secured to the tip end body 12. The connection tube 37 is made of electrically insulating material.

With this structure, the coil pipe 36b which contacts the bendable section 4 and metallic members inside the insertion section 1 is electrically insulated with respect to the tip end body 12 and the operation wire 22. The operation wire 22 is electrically conductive with respect to the tip end body 12 and the direction setting table 5, but is electrically insulated with respect to the bendable section 4, metal members inside the insertion section 1 and the coil pipe 36b.

Figure 7:
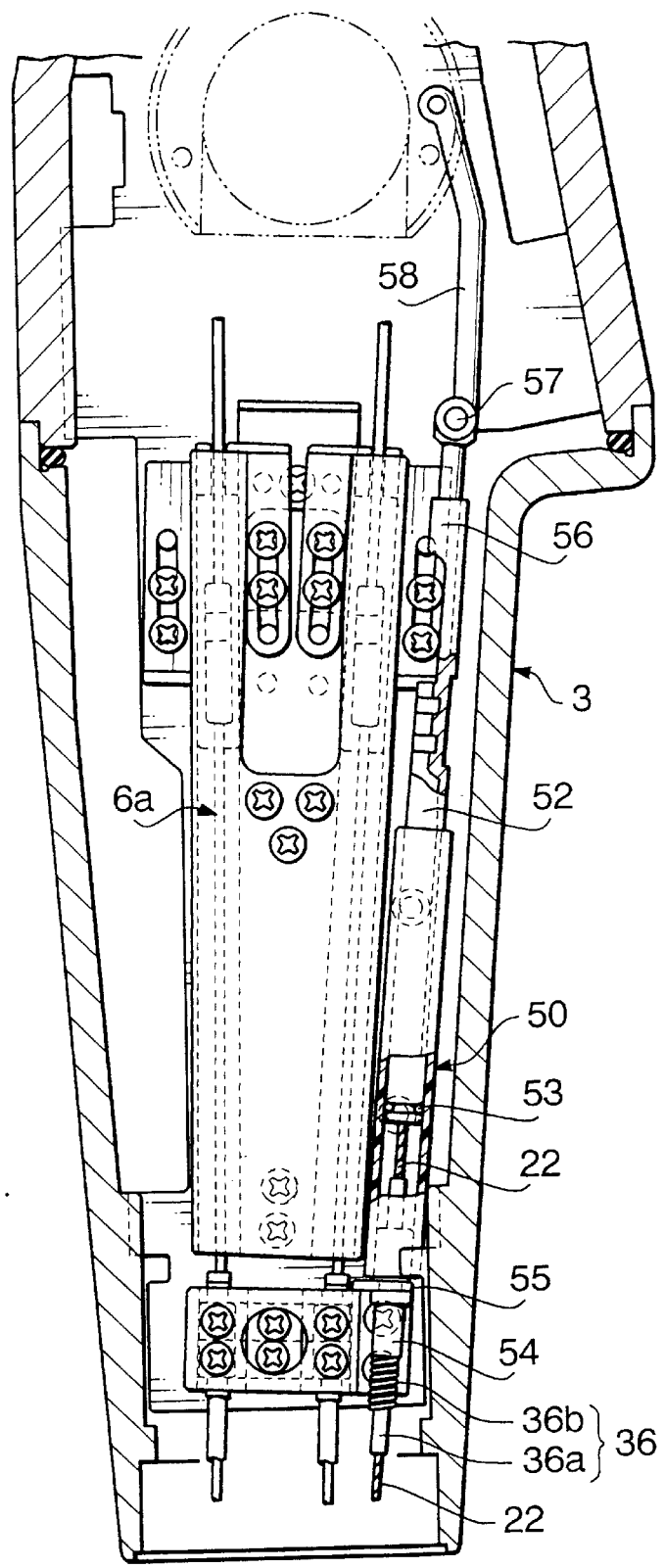
FIG. 7 is a partially cross sectional side view showing an inner structure of the operation unit of the endoscope.

FIG. 7 shows an inner structure of the operation unit 3. In FIG. 7, 6a denotes a bending mechanism which moves the wire 43 upon operation of the bending knob 6. A direction setting mechanism 50 which is operated by the knob 8 is provided along the bending mechanism 6a.

Figure 8:
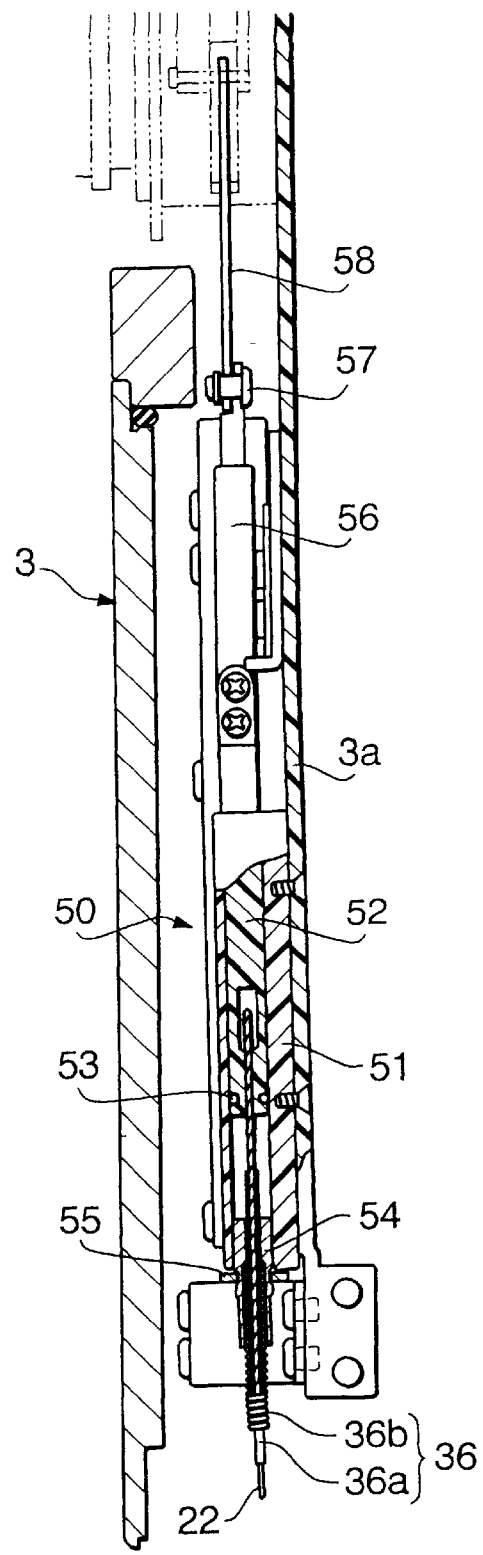
FIG. 8 is a partially cross sectional front view showing the inner structure of the operation unit.

FIG. 7 shows a partially cross sectional side view of the direction setting mechanism 50, and FIG. 8 shows a partially cross sectional front view thereof. In FIG. 8, 51 denotes a guide tube formed of electrically insulating material, which is fixed to a frame 3 of the operation unit 3 with screws.

A wire driving rod 52 made of electrically insulating material is movably inserted in the guide tube 51. A proximal end of the operation wire 22 which is drawn from the proximal end of the wire guide 36 is secured to the wire driving rod 52.

The outer circumference of the wire driving rod 52 is fitted in the guide tube 51, and an O-ring 53 made of elastic material is fitted on the wire driving rod 52 such that it is slightly deformed. Due to deformation of the O-ring 53, a resistance is generated against rotational movement of the wire driving rod 52 with respect to the guide tube 51. Thus, the wire rod 52 does not rotate when it is operated to move along the axis thereof.

On the other end of the wire driving rod 52, a connection tube 56 is connected with screws, and further, a link member 58 is rotatably connected with a pin 57. The link member 58 is driven by the knob 8.

Figure 9:
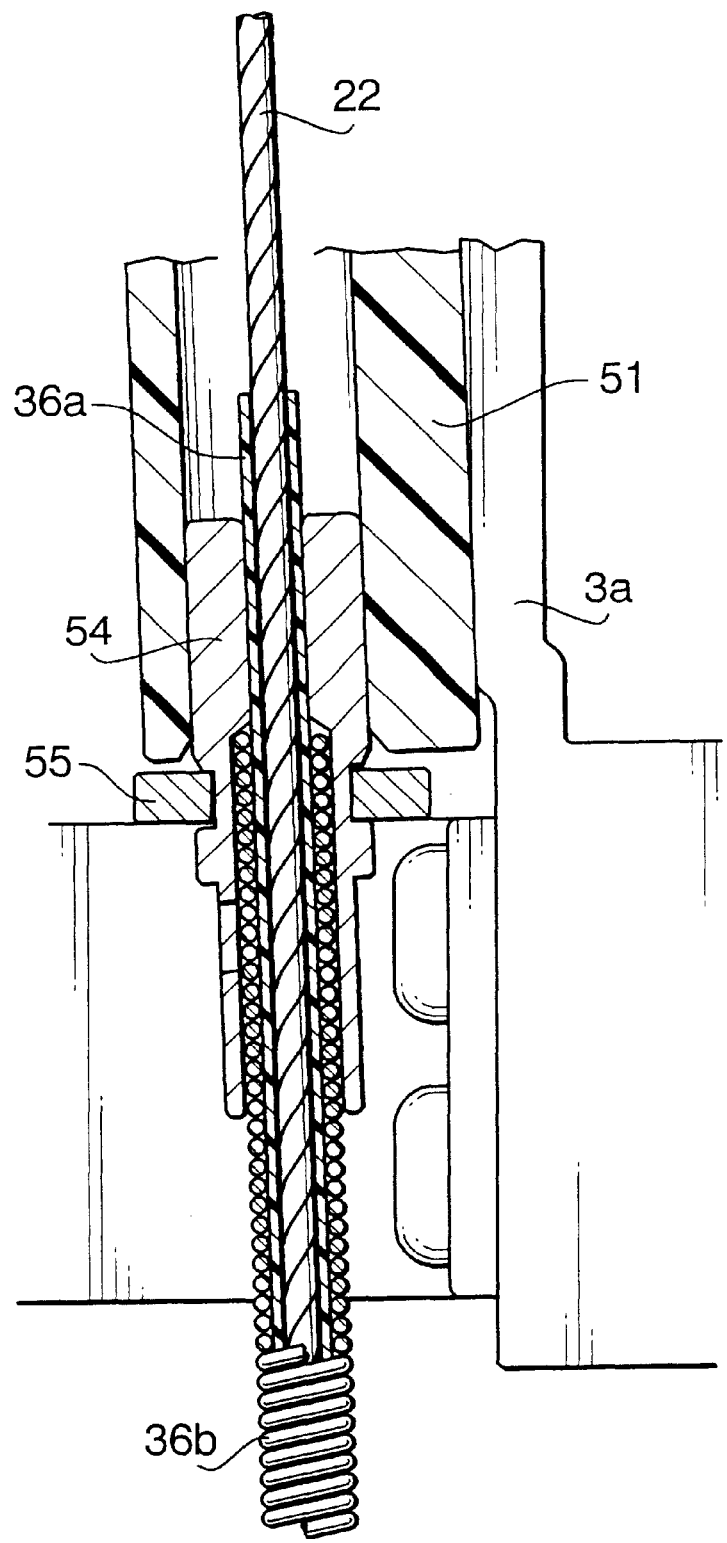
FIG. 9 is an enlarged cross sectional view of a proximal end portion of the wire guide.

A metal stopper 54 is secured to the proximal end of the coil pipe 36b of the wire guide 36 with soldering as shown in an enlarged view of FIG. 9. The stopper 54 is hooked by a support member 55 secured on the frame 3a.

The end portion of the insulating tube 36a of the wire guide 36 protrudes from the end of the coil pipe 36 by a predetermined amount (e.g., a few millimeters through a few centimeters), and electrical insulation between the operation wire and the metal members such as the stopper 54 in the operation unit 3 is ensured.

With this structure, when the knob 8 is operated, the operation wire 22 is moved forwardly/reversely inside the wire guide 36 via the driving mechanism 50. Then, the direction setting table 5 located at the tip end 1a of the insertion section 1 rocks and the direction in which the tip end 100a of the treatment instrument 100 protrudes can be changed.

As described above, the operation unit 3 is electrically insulated with respect to the metal members (e.g., the tip end body 12, the direction setting table 5 and the like) provided at the tip end 1a of the insertion section 1. Therefore, when a high frequency current tool is used as the treatment instrument 100, and the high frequency leaks onto the direction setting table 5, the electrical current does not flow across the operation unit 3, and accordingly, the operator will not suffer burns due to the high frequency current.

Further, since the direction setting table and/or the members around the direction setting table can be formed as single metal members, sufficient strengths can be ensured, and manufacturing process can be eased, and is highly suitable for practical use.

The present disclosure relates to the subject matter contained in Japanese Patent Application No. HEI 11-173491, filed on Jun. 21, 1999, which is expressly incorporated herein by reference in its entirety.

What is claimed is:

1. An endoscope, comprising:

an operation unit provided with at least one operation member;

an insertion section configured to be inserted in a human cavity, the operation unit being connected with a proximal end of the insertion section;

a metal body member provided at a distal end portion of the insertion section;

a metal direction setting table provided on the body member, the direction setting table adjusting a direction of a treatment accessory;

an insulation member provided between the distal end of the insertion section and the body member so that the body member is insulated from the distal end of the insertion section;

an insulating cap that covers the entire body member and the direction setting table except for an opening through which the treatment accessory protrudes to an exterior;

an operation wire that is axially movable upon operation of the operation member, the operation wire being connected to the direction setting table so that the direction setting table is moved in accordance with an operation of the operation member.

2. The endoscope according to claim 1, said operation wire being surrounded by electrically insulating material, and said operation wire being electrically insulated with respect to the operation member of said operation unit.

3. The endoscope according to claim 1, wherein said operation wire is connected to said operation member via a link mechanism, said link mechanism including a link member connected to said operation member, and a rod member connecting said link member and said operation wire, said rod member being fitted in and guided by a tube member so as to move in an axial direction thereof.

4. The endoscope according to claim 3, wherein said tube member is formed of insulating material.

5. The endoscope according to claim 4, wherein a proximal end of said wire is secured to said rod member, said rod member being made of insulating material.

6. The endoscope according to claim 3, wherein an O-ring is provided on said rod member, said O-ring being deformed to have an elliptic shape, a rotational movement of said rod member with respect to said tube member being prevented due to the elliptic shape of said O-ring.

* * * * *